(12) United States Patent
Huttner

(10) Patent No.: US 8,761,858 B1
(45) Date of Patent: Jun. 24, 2014

(54) METHOD OF ATTACHING ELECTRODE PATCHES TO AN INFANT

(71) Applicant: Bionix Development Corporation, Toledo, OH (US)

(72) Inventor: James J. Huttner, Sylvania, OH (US)

(73) Assignee: Bionix Development Corporation, Toledo, OH (US)

( * ) Notice: Subject to any disclaimer, the term of this patent is extended or adjusted under 35 U.S.C. 154(b) by 0 days.

(21) Appl. No.: 13/626,952

(22) Filed: Sep. 26, 2012

Related U.S. Application Data

(60) Provisional application No. 61/539,027, filed on Sep. 26, 2011.

(51) Int. Cl.
*A61B 5/0408* (2006.01)
*A61B 5/053* (2006.01)

(52) U.S. Cl.
USPC ............................ 600/388; 600/390; 600/393

(58) Field of Classification Search
CPC .. A61B 5/0408; A61B 5/04085; A61B 5/6808
USPC ......................................... 600/388, 390, 393
See application file for complete search history.

(56) References Cited

U.S. PATENT DOCUMENTS

| | | | | |
|---|---|---|---|---|
| 4,026,278 | A * | 5/1977 | Ricketts et al. | 600/390 |
| 6,198,955 | B1 * | 3/2001 | Axelgaard et al. | 600/391 |
| 6,970,731 | B1 * | 11/2005 | Jayaraman et al. | 600/388 |
| 7,173,437 | B2 | 2/2007 | Hervieux | |
| 7,245,956 | B2 | 7/2007 | Matthews et al. | |
| 7,319,895 | B2 * | 1/2008 | Klefstad-Sillonville et al. | 600/388 |
| 7,324,841 | B2 | 1/2008 | Reho et al. | |
| 7,539,532 | B2 * | 5/2009 | Tran | 600/509 |
| 7,680,523 | B2 | 3/2010 | Rytky | |
| 7,966,052 | B2 * | 6/2011 | DeFusco et al. | 600/386 |
| 8,032,199 | B2 | 10/2011 | Linti et al. | |
| 8,050,733 | B2 | 11/2011 | Rytky | |
| 8,082,762 | B2 | 12/2011 | Burr | |

(Continued)

FOREIGN PATENT DOCUMENTS

| | | |
|---|---|---|
| WO | 2009043196 A1 | 4/2009 |
| WO | 2011131235 A1 | 10/2011 |

OTHER PUBLICATIONS

Ottenbacher J. et al.: "Intergration of a Bluetooth Based ECG System into Clothing" Proceedings of the Eighth International Symposium on Wearable Computers (ISWC 2004), Oct. 31, 2004 m pp. 186-187, XPO10749653 ISBN: 978-0-7695-2186-2.

(Continued)

*Primary Examiner* — Lee S Cohen
(74) *Attorney, Agent, or Firm* — Marshall & Melhorn, LLC

(57) ABSTRACT

A method of positioning electrodes on a patient for detecting a cardiac waveform and/or a respiratory waveform includes providing a plurality of electrodes having an upper and lower surface, the lower surface having electrically conductive properties suitable to detecting a cardiac and/or respiratory waveform and substantially no adhesive properties, and the upper surface being covered in part with a material having adhesive or affixative properties. A first electrode is placed under a garment worn by the patient in the region of the left lower abdomen/inguinal region, such that the adhesive surface thereof affixes to the underside of the garment. A second electrode is placed under a garment in the region of the right lower abdomen/inguinal region, such that the adhesive surface thereof affixes to the underside of the garment.

15 Claims, 6 Drawing Sheets

(56) References Cited

U.S. PATENT DOCUMENTS

| | | |
|---|---|---|
| 8,214,044 B2 | 7/2012 | Dal Molin |
| 8,260,427 B2 | 9/2012 | Thramann et al. |
| 8,340,740 B2 | 12/2012 | Holzer et al. |
| 8,386,009 B2 | 2/2013 | Lindberg et al. |
| 2004/0138546 A1 | 7/2004 | Reho et al. |
| 2005/0010096 A1 | 1/2005 | Blackadar |
| 2006/0100530 A1* | 5/2006 | Kliot et al. ............ 600/483 |
| 2006/0258916 A1* | 11/2006 | Pietersen ............... 600/301 |
| 2007/0073131 A1 | 3/2007 | Ryu et al. |
| 2007/0299325 A1 | 12/2007 | Farrell et al. |
| 2009/0227857 A1* | 9/2009 | Rowe et al. ............ 600/392 |
| 2010/0328075 A1* | 12/2010 | Rahamim et al. ........ 340/573.1 |
| 2013/0041272 A1 | 2/2013 | Arredondo |
| 2013/0072777 A1 | 3/2013 | Tremblay |

OTHER PUBLICATIONS

Paradisco R. et al.: "A Wearable Health Care System Based on Knitted Integrated Sensonrs" IEEE Transactions on Information Technology in Biomedicine, vol. 9, No. 3, Sep. 1, 2005, pp. 337-344, XP011138580 ISSN: 1089-7771.

* cited by examiner

SKIN-CONTACT SIDE

NON SKIN-CONTACT SIDE

METHOD OF ATTACHING ELECTRODE PATCHES TO AN INFANT

CROSS-REFERENCE TO RELATED APPLICATIONS

This application is claiming the benefit, under 35 U.S.C. §119(e), of the provisional application filed Sep. 26, 2011 under 35 U.S.C. §111(b), which was granted Ser. No. 61/539,027. This provisional application is hereby incorporated by reference in its entirety.

BACKGROUND OF THE INVENTION

Many infants, especially premature infants, require hospitalization in an intensive care unit for medical conditions surrounding their birth. Examples of disease conditions requiring such ICU care are sepsis, respiratory distress, low blood sugar, and those requiring surgical intervention, to name just a few. Premature infants are more likely to require intensive care hospitalization than their term counterparts.

Infants hospitalized in the intensive care setting are monitored closely for heart rate, respiratory rate, pulse oximetry, and other vital signs. Of these, heart rate and respiratory rate are most often monitored using an EKG monitor. An EKG monitor displays heart rate and rhythm by detecting electrical signals coming from an infant's heart. Respiratory rate is displayed, as well, by detecting electrical impedance changes in the infant's chest wall. These electrical signals are picked up by electrodes affixed to the chest wall of the infant.

Typically, three electrodes are used for routine monitoring purposes. By convention, one electrode is placed over the upper right chest wall, another over the upper left chest wall, and one over the lower left chest wall. However, different electrode placement patterns can provide adequate EKG and respiratory rate detection for monitoring purposes, as long as the current path is sufficiently long to provide sufficient signal amplitude, and as long as convention is followed to produce wave-forms of the correct shape and vector.

The most critical factors in obtaining a satisfactory EKG tracing are skin resistance and electrode/skin contact. Current EKG electrodes use ionic, conductive materials designed to minimize skin impedance in order to acquire an adequate signal. State of the art electrodes have a highly conductive hydrogel or paste to maximize signal detection. Conductive hydrogels are also adhesive in nature. The hydrogel composition can be manipulated to enhance its adhesive properties to produce a sticky electrode that maintains tight fixation to the patient's chest to minimize noise from chest wall and electrode movement, and to prevent the electrode from detaching and interrupting the signal.

Other electrodes utilize a non-adhesive conductive paste to reduce skin resistance and detect the EKG signal; most often these electrodes are constructed with the conductive paste portion centered in an adhesive pad that provides for tight adherence to the patient's skin. All-metal EKG electrodes exhibit good conductivity, but must be securely attached to the skin to ensure good signal pickup and minimize motion artifact and detachment. Metal electrodes are usually simply taped to the skin to provide good electrode/skin contact.

A well recognized problem in the neonatal intensive care unit (NICU) is that often the adhesive nature of electrodes (either sticky hydrogel or adhesive backing) causes significant skin breakdown and injury. This problem is especially severe in the premature infant, whose thin skin is very fragile and subject to trauma. Also, chemical dermatitis caused by the skin adhesive can be unpredictable, leading to contact dermatitis and bullous skin lesions. Placement and removal of EKG electrode patches has been found to be a significant source of skin trauma in these patients; the skin tears and abrasions caused by electrode patch removal cause significant pain, and expose the baby to life threatening infections.

The current invention is designed to alleviate the problem of skin injury in newborn infants through a novel method of attaching EKG electrodes without the use of adhesive gels or materials.

SUMMARY OF THE INVENTION

The current invention describes novel EKG electrodes, and a novel method of placing EKG electrodes on the newborn infant for the purposes of displaying or recording a cardiac rhythm and or respiratory rate.

Current convention utilizes three electrodes for routine monitoring purposes in the NICU. By convention, one electrode is placed over the upper right chest wall, another over the upper left chest wall, and one over the lower left chest wall. However, different electrode placement patterns can provide adequate EKG and respiratory rate detection for monitoring purposes, as long as the current path is sufficiently long to provide sufficient signal amplitude, and as long as convention is followed to produce wave-forms of the correct shape and vector.

Currently available EKG electrodes are constructed using an adhesive material to maintain good skin contact and proper positioning of the EKG patch. The adhesive material may be in the form of an adhesive hydrogel, or may be an adhesive foam or fabric tape material. Low impedance skin contact, essential for proper sensing of the cardiac rhythm and respiratory rate is provided by a conductive hydrogel, gel, or paste that couples the electrode to the skin. The typical construction of an EKG electrode surrounds this conductive medium with the adhesive material, although some use only the adhesive properties of the hydrogel itself to maintain good electrode/skin contact.

The current invention involves the use of EKG electrodes that have a conductive portion that has the properties of low impedance and high conductivity to adequately detect and transmit the EKG signal, but do not have any skin contact adhesive materials or properties that might cause skin breakdown or injury. The conductive portion may be comprised of non-adhesive conductive pastes, gels, or hydrogels, or may be dry, metalized or conductive carbon electrodes. Alternatively, non-contact, capacitively coupled electrodes may be utilized to detect the EKG signal.

A problem with non-adhesive EKG electrodes is that they are subject to motion artifact and positional failure (i.e. falling off the chest wall). To prevent these problems and to ensure good electrode/skin contact, the EKG electrodes described in this invention have an adhesive means on their outer, non-skin contact surface. This adhesive means on the outer, non-skin contact surface of the EKG electrodes would adhere to the inner surface of the patient's diaper to serve to keep the electrodes securely in place, while the diaper itself would hold the EKG electrodes firmly against the infant's skin. Such adhesive means might take the form of a standard removable adhesive, or alternatively a low-profile hook-and-loop (Velcro) type material might be used.

In use, at least two EKG electrodes would be placed in the lower abdominal/inguinal regions—one on the left and one on the right—under the upper portion of the diaper. The adhesive or Velcro-like surface of the EKG electrodes would adhere to the inner surface of the diaper to serve to keep the electrodes securely in place, while diaper itself would hold the EKG electrodes firmly against the infant's skin.

The third electrode is constructed similarly to the other two, having a skin contact surface with conductive gel or paste, but no skin adhesive properties. The outer, non-skin contact surface of this electrode is designed with an adhesive or Velcro-like surface, and is intended to be held in place by affixing it to the underside of the infant's garment, or wrap. Alternatively, a sash-like strip of non-wicking material may be provided that extends from the front of the diaper, across the infant's shoulder, and down to the back of the diaper. Alternatively, a strip of material fashioned into a wrist or arm-band might be used. The third electrode would then be affixed to the underside of this sash in the area of the right shoulder or under the wrist or arm-band in a manner similar to that used to affix the other two electrodes in the diaper area.

The three electrodes would be connected in the usual fashion to the NICU monitor unit to display cardiac rhythm and respiratory rate.

There is also the possibility that an adequate EKG signal tracing could be obtained from only two EKG electrodes instead of the typical three-electrode set-up. In that case, only the two electrodes affixed to the underside of the diaper (as described above) would be needed and used.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

Figure 1:
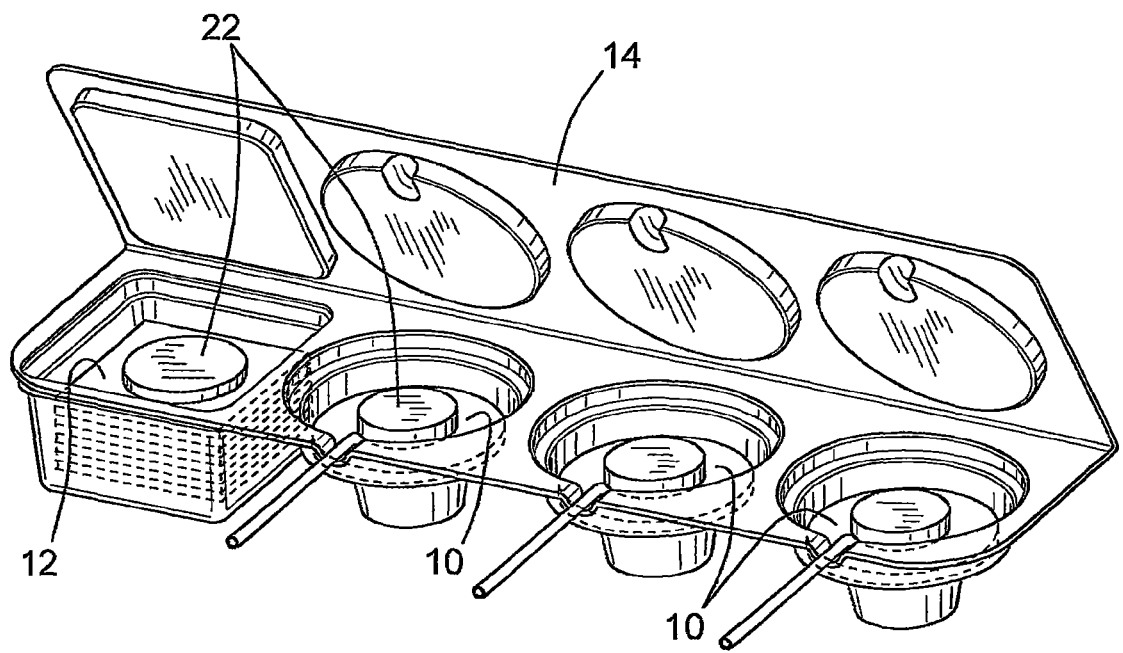
FIG. 1 is a perspective of an embodiment of a package containing electrodes and sash or armband for use in embodiments of the method of the invention.

FIG. 1 shows a conceptual drawing of three non-adhesive electrodes, generally referenced by numeral 10, and the sash 12, as packaged using plastic clamshell packaging 14. It is understood that alternate packaging means may be used without deviating from the intent of the invention.

Figure 6:
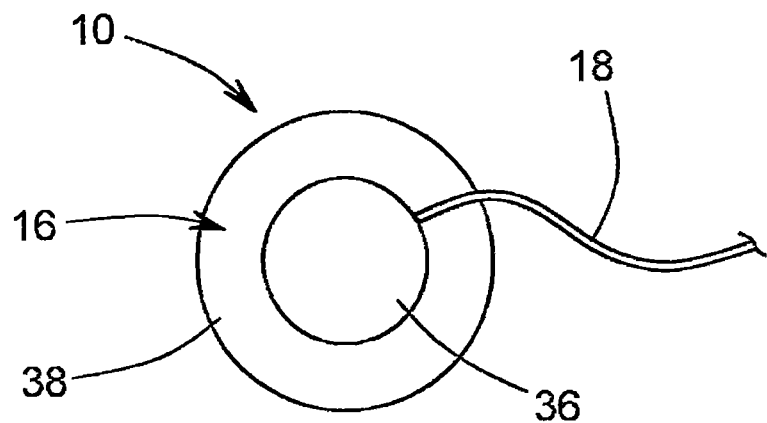
FIG. 6 is a view of an embodiment of an electrode for use in embodiments of the invention.
Figure 6:
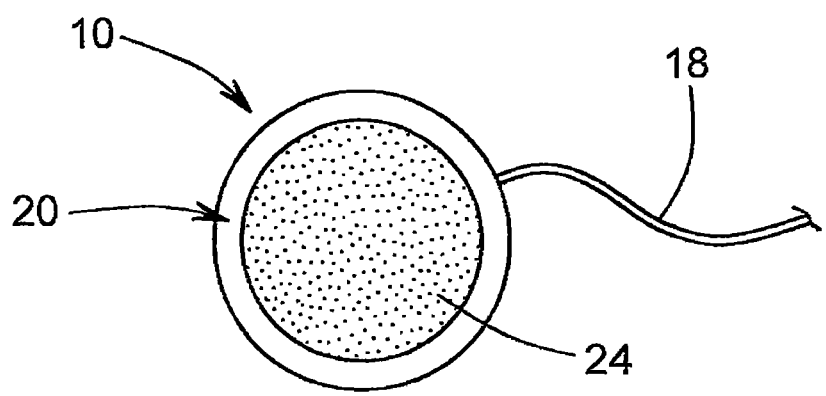

As best seen in FIG. 6, the lower or skin-contact surfaces 16 of the electrodes 10 have a non-adhesive conductive surface for detection of the cardiac and/or respiratory signals. This may be a solid or wet hydrogel material, conductive paste, or dry carbon film. Other conductive materials may also be used to provide the electrical properties necessary to optimum electrode performance of the electrode. Leads 18 extend from the electrodes as shown in this drawing. Pre-attached leads are commonly included with NICU electrode sets for ease of use; however, electrodes without pre-attached leads may also be used without deviating from the intent of the invention.

The upper or non-skin contact surface 20 of each of the electrodes 10 is shown in FIG. 1 covered with a Velcro-like material 22 for the purpose of affixing to the material of a garment worn by the patient, such as a diaper or the sash 12. As an alternative, an adhesive material 24 may be provided on the non-skin contact surface 20 of each of the electrodes 10 as a substitute for the Velcro-like material as a means to affix the electrodes 10 to a patient garment without deviating from the intent of the invention.

In FIG. 1, the sash 12 is shown folded in its storage compartment. In use, the sash 12 would be unfolded, and be formed of a strip of materially, typically approximately 14 inch long, with Velcro-like tabs 22 or adhesive tabs at either end. The Velcro-like or adhesive material tabs are intended to affix the sash 12 to the diaper or other garment in order to hold it in place over the patient's shoulder. This can be seen, for example, schematically in FIG. 2. The material of the sash 12 is designed to affix to the Velcro or adhesive on the non-skin contact side 20 of an electrode 10, in order to hold it in position.

Figure 2:
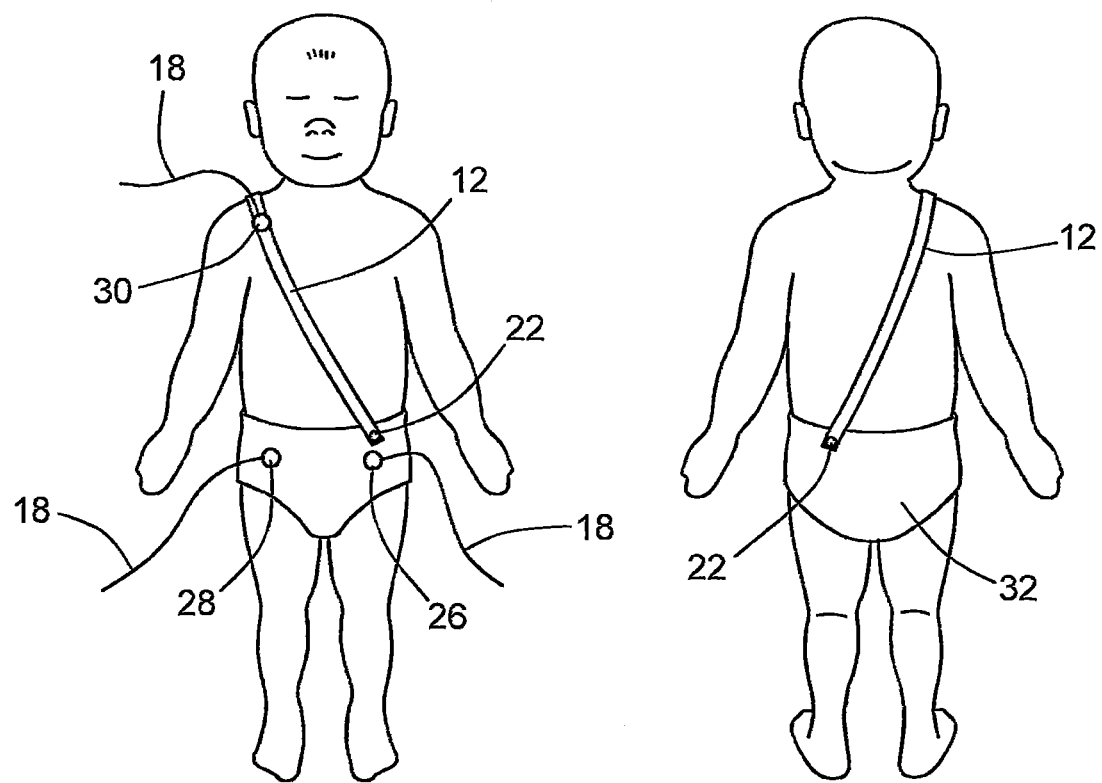
FIG. 2 is a schematic view of electrodes and sash as used on an infant in accordance with an embodiment of the invention.

FIG. 2 shows a line drawing of the electrodes 10 and sash 12 as they would be used in accordance with an embodiment of the method of the invention. FIG. 2 shows first and second electrodes 26, 28 placed under a diaper 32 worn by a patient in the lower left and right abdominal/inguinal region, respectively, and a third electrode 30 placed under the sash 12 in the region of the upper right chest of the patient. An electrode arrangement such as this has been shown to provide adequate cardiac and respiratory waveforms. Also shown in FIG. 2 is the sash 12, and how it would affix to the diaper 32 and how it would be placed around the infant patient in order to maintain the position of the third electrode 30. It is understood that the third electrode 30 could be affixed to any garment the child might wear, such as a t-shirt, a onesie or similar garment, without deviating from the intent of the invention.

Figure 3:
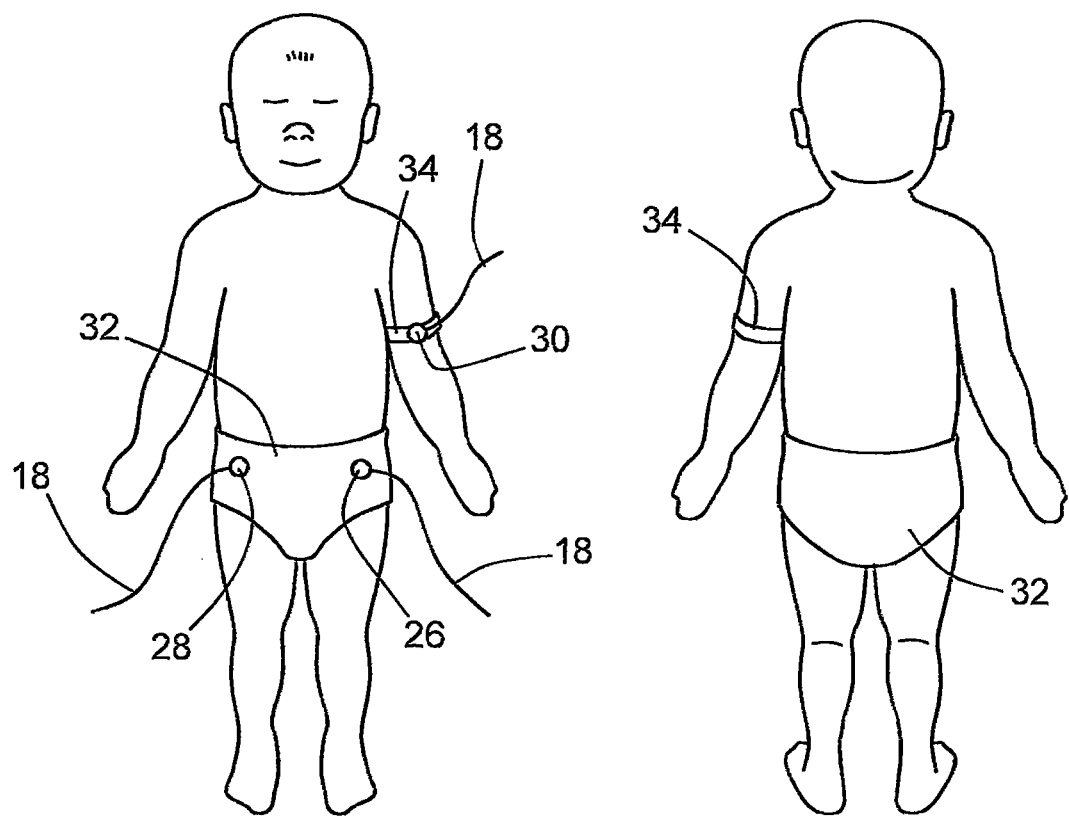
FIG. 3 is a schematic view of electrodes and armband as used on an infant in accordance with an alternate embodiment of the invention.

FIG. 3 shows a line drawing of the electrodes 26, 28, 30 and an arm-band 34 as they would be used in accordance with another embodiment of the method of the invention. FIG. 3 shows the first and second electrodes 26, 28 placed under the diaper 32 in the lower left and right abdominal/inguinal regions, and the third electrode 30 placed under an arm-band 34 in the region of the upper left arm. An electrode arrangement such as this has been shown to provide adequate cardiac and respiratory waveforms. It is understood that the third electrode 30 could affixed to an "arm"-band around any portion of the infant's left or right arms, or either leg, as long as an adequate EKG wave-form was obtained, without deviating from the intent of the invention.

Figure 4:
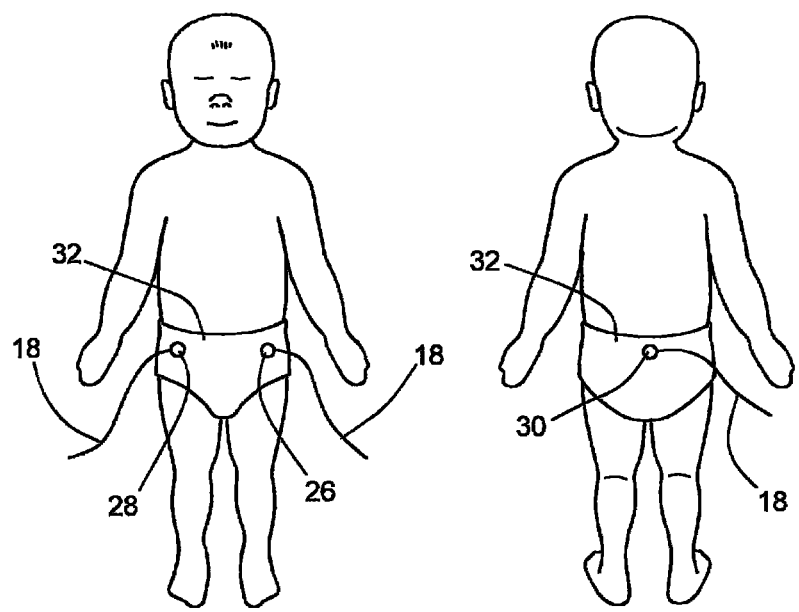
FIG. 4 is a schematic view of electrodes as used on an infant in accordance with another alternate embodiment of the invention.

FIG. 4 shows a line drawing of the electrodes 26, 28 as they would be used in accordance with a further embodiment of the method of the invention, in which a three-electrode protocol is employed employing the first and second electrodes 26, 28 as abdominal electrodes and the third electrode 30 as a posterior electrode. The first and second electrodes 26, 28 would be placed under the diaper 32 in the lower left and right abdominal/inguinal regions. The third electrode 30 would be placed in a posterior location under the diaper 32 in the region of the upper buttocks.

Figure 5:
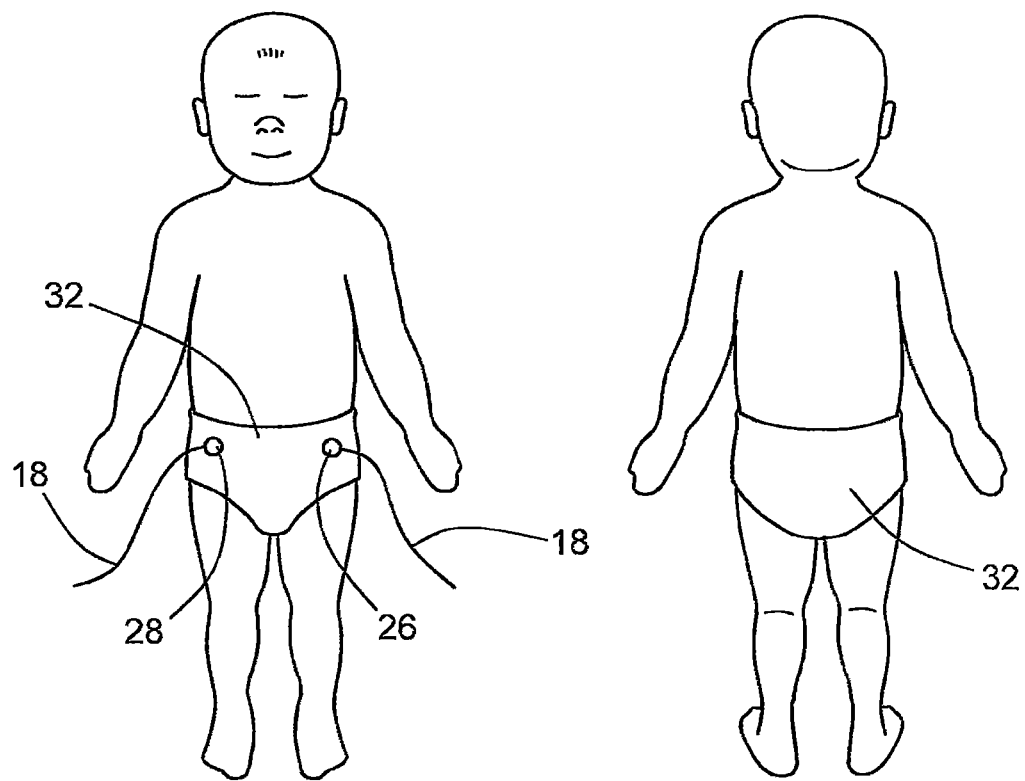
FIG. 5 is a schematic view of electrodes as used on an infant in accordance with a further embodiment of the invention.

FIG. 5 shows a line drawing of the first and second electrodes 26,28 as they would be used in accordance with still another embodiment of the method of the invention using a two-electrode protocol. The first and second electrodes 26, 28 would be placed under the diaper 32 in the lower left and right abdominal/inguinal regions. A third electrode would not be utilized in accordance with this embodiment the invention.

As noted above, FIG. 6 shows the construction of a preferred embodiment of the electrode 10 of this invention. The electrode 10 has a lower, skin-contact side 16. At the center of this side 16 of the electrode 10 is a non-adhesive conductive pad 36. This may be composed of a non-adhesive conductive gel or hydrogel, a conductive paste, a conductive liquid-soaked sponge or pad, or a dry, conductive metallic or carbon pad. An electrode wire or lead 18 is attached to this conductive pad 36 and is shown; it is understood that this wire will have the standard connectors (not shown) allowing it to be connected to a heart rate monitor or the like. The conductive pad 36 is shown secured on a non-adhesive backing material 38. The backing material 38 is provided for structural strength and manufacturability, and may be composed of cloth, plastic, foam, or other suitable material.

The upper, non skin-contact side 20 of the preferred embodiment of the electrode 10 is covered to a significant amount by an adhesive surface material 24. This adhesive surface material may include a standard, non-drying, releasable adhesive or tape. Alternatively, an affixing means may be provided, such as a piece of a Velcro-type hook-and-loop material 22 designed to affix securely to the non-woven material of a diaper. It is understood that any sufficiently adhesive or affixing material may be used for this portion of the electrode 10 for this purpose without compromising the intent of the invention. Again, the non-adhesive backing material 38 and lead 18 are shown.

In accordance with the provisions of the patent statutes, the invention has been described in what is considered to represent its preferred embodiments. However, it should be noted that the invention could be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A method of positioning electrodes on a patient for detecting a cardiac waveform and/or a respiratory waveform, comprising the steps of:
   a. providing a plurality of electrodes having an upper and lower surface,
      i. said lower surface having electrically conductive properties suitable to detecting a cardiac and/or respiratory waveform,
      ii. said lower surface having substantially no adhesive properties, and
      iii. said upper surface being covered in part with a material having adhesive or affixative properties;
   b. placing a first electrode under a garment worn by the patient in the region of the left lower abdomen/inguinal region, such that the adhesive surface of said first electrode affixes to said garment;
   c. placing a second electrode under said garment worn in the region of the right lower abdomen/inguinal region, such that the adhesive surface of said electrode affixes to said garment; and
   d. wherein the lower surface of each electrode comprises a skin-contact surface that is brought into contact with the skin of the patient so as to be able to detect a cardiac waveform and/or a respiratory waveform.

2. The method of claim 1, further comprising placing a third electrode in the region of the patient's right arm, left arm, right leg, left leg, upper left chest, upper right chest, left shoulder, or right shoulder, underneath a second garment worn by the patient, such that the upper adhesive surface of said electrode affixes to said second garment, wherein the lower surface of the third electrode comprises a skin-contact surface that is brought into contact with the skin of the patient, and wherein the second garment may be the same garment or a different garment from under which the first and second electrodes are placed.

3. The method of claim 2, wherein the second garment comprises a strip of material having adhesive tabs on either end for affixing the second garment to the garment under which the first and second electrodes are placed.

4. The method of claim 2, wherein the second garment comprises a strip of material having adhesive tabs on either end for affixing an end of the second garment to the opposite end of the second garment to form a limb or torso encircling band.

5. The method of claim 1, further comprising placing a third electrode under the garment in the patient's lower back/lumbar/sacral spine region.

6. The method of claim 1, wherein only the first and second electrodes are utilized to produce an adequate cardiac and respiratory waveform.

7. The method of claim 1, wherein the garment is comprised of a diaper.

8. The method of claim 1, wherein the electrodes have a non-adhesive, conductive gel or hydrogel on the skin-contact surface for detecting a cardio-respiratory signal.

9. The method of claim 1, wherein the electrodes have a non-adhesive, conductive paste on the skin-contact surface for detecting a cardio-respiratory signal.

10. The method of claim 1, wherein the electrodes have a non-adhesive, conductive carbon material on the skin-contact surface for detecting a cardio-respiratory signal.

11. The method of claim 1, wherein the electrodes have a non-adhesive, conductive metal or metalized material on the skin-contact surface for detecting a cardio-respiratory signal.

12. The method of claim 1, wherein the electrodes have capacitive coupling as a means for detecting a cardio-respiratory signal.

13. The method of claim 1, wherein the garment is comprised of an infant T-shirt or onesie.

14. The method of claim 1, wherein the adhesive on the non-skin contact surface of the electrodes is comprised of a hook-and-loop material designed to affix to a non-woven material forming at least a portion of said garment.

15. The method of claim 1, wherein the adhesive on the non-skin contact surface of the electrodes is comprised of a standard, non-drying, releasable adhesive or tape.

\* \* \* \* \*